United States Patent
Howarth et al.

(10) Patent No.: US 7,392,720 B2
(45) Date of Patent: Jul. 1, 2008

(54) APPARATUS FOR THE ASSESSMENT OF THE CONDITION OF FRUITS AND VEGETABLES

(75) Inventors: Matthew Scott Howarth, Clovis, CA (US); Richard Allen, Norwich (GB)

(73) Assignee: Sinclair International Limited, Bowthorpe, Norwich, Norfolk (GB)

( * ) Notice: Subject to any disclaimer, the term of this patent is extended or adjusted under 35 U.S.C. 154(b) by 240 days.

(21) Appl. No.: 10/507,455

(22) PCT Filed: Mar. 12, 2003

(86) PCT No.: PCT/GB03/01011

§ 371 (c)(1),
(2), (4) Date: Jul. 21, 2005

(87) PCT Pub. No.: WO03/079005

PCT Pub. Date: Sep. 25, 2003

(65) Prior Publication Data

US 2006/0048588 A1    Mar. 9, 2006

(30) Foreign Application Priority Data

Mar. 12, 2002   (GB) ................................ 0205667.9

(51) Int. Cl.
*G01N 33/02* (2006.01)
(52) U.S. Cl. .......................... 73/866.5; 73/661; 73/866
(58) Field of Classification Search ........... 73/661–662, 73/866, 866.5; 426/231; 99/493, 451
See application file for complete search history.

(56) References Cited

U.S. PATENT DOCUMENTS

| | | | | |
|---|---|---|---|---|
| 2,784,495 | A | * | 3/1957 | Croshier ................... 33/501.05 |
| 3,470,737 | A | * | 10/1969 | Fridley ........................... 73/81 |
| 4,061,020 | A | * | 12/1977 | Fridley et al. ................... 73/81 |
| 4,217,164 | A | * | 8/1980 | La Mers ...................... 156/541 |
| 4,732,662 | A | * | 3/1988 | Holscher ..................... 600/354 |
| 5,524,030 | A | * | 6/1996 | White et al. ................. 376/260 |
| 5,691,473 | A | | 11/1997 | Peleg ........................... 73/573 |
| 6,857,317 | B2 | * | 2/2005 | Sakurai .................. 426/231 X |
| 6,998,559 | B2 | * | 2/2006 | De Baerdemaeker et al. .......................... 209/590 |

FOREIGN PATENT DOCUMENTS

| | | |
|---|---|---|
| WO | WO 97/27006 | 7/1997 |
| WO | WO 98/40737 | 9/1998 |
| WO | WO 98/52037 | 11/1998 |
| WO | PCT/GB03/01011 | 9/2003 |

* cited by examiner

Primary Examiner—Thomas P. Noland
(74) Attorney, Agent, or Firm—Barlow, Josephs & Holmes, Ltd.

(57) ABSTRACT

Apparatus for assessing the condition of fruit or vegetables comprises a transducer (22) which is brought into contact with the surface of fruit or vegetable (12) in a tapping motion. The transducer (22), where it contacts the fruit or vegetable's surface is generally curved in shape to ensure accuracy of measurement over a relatively wide range of angles of impact with the fruit or vegetable (12). The transducer (22) can be delivered to and away from the fruit or vegetable surface by an air controlled bellows arrangement.

20 Claims, 2 Drawing Sheets

APPARATUS FOR THE ASSESSMENT OF THE CONDITION OF FRUITS AND VEGETABLES

This invention relates to improvements in or relating to apparatus for the assessment of the condition of fruit and vegetables.

In our co-pending published PCT Application No. WO 98/52037 there is disclosed an assembly for measuring the condition of fruit and vegetables in which an expandable resilient bellows arrangement, having an active or passive sensor mounted therein, can be expanded so as to bring the sensor into contact with, or adjacent to, an item of fruit or vegetables whereby the sensor can react to a property of the fruit or vegetable (e.g. ripeness or firmness) and produce a signal related to that property. The bellows assembly can then be retracted away from the fruit or vegetable. Published PCT Application No. WO 98/40737 also discloses a similar arrangement.

A problem with these arrangements is that, for consistent measurement, it is necessary to ensure that the sensor moves towards the item of fruit or vegetable substantially perpendicularly. If the sensor moves at an angle to the fruit or vegetable then inaccurate results can be obtained.

It is an object of the present invention to provide an arrangement of the type disclosed in the earlier applications mentioned above in which it is possible to obtain a more consistent measurement over a relatively larger angular range of impact between the sensor and the surface of the fruit or vegetable being tested.

Thus and in accordance with the present invention therefore there is provided apparatus for measuring the condition of fruit and vegetables comprising plunger means moveable into and out of contact with a surface of an item of fruit or vegetable, said plunger means carrying a transducer which is brought into contact with an item of fruit or vegetable, the transducer reacting to a property of said fruit or vegetable to produce an output signal related to that property characterised in that at least a part of said plunger means or transducer which contacts said item of fruit or vegetable is of generally curved shape.

With this arrangement, the curved shape of the plunger or transducer ensures a consistently accurate output signal related to the condition of the fruit or vegetable over a relatively wide range of angles of impact of the plunger or transducer on the surface of the fruit or vegetable.

Preferably said plunger means is mounted in a resilient bellows assembly, for movement therewith, the bellows assembly being capable of expansion under the action of pressurised air and retraction by the application of a vacuum. Alternatively any other form of means can be used as desired or appropriate to move the plunger or transducer into and out of contact with an item of fruit or vegetable.

Most preferably the transducer comprises an active transducer and may, in a preferred embodiment comprise a piezoelectric sensor. It will be appreciated that the transducer can take any appropriate form as desired, which is capable of measuring the condition e.g. ripeness, firmness or otherwise of the item of fruit or vegetable with which it is brought into contact.

Preferably the plunger means or transducer is generally hemispherical in shape at least at the part thereof which contacts the fruit or vegetable surface.

The invention will now be described further by way of example only and with reference to the accompanying drawings in which:

FIG. 1 shows an assembly 10 which can be moved into and out of contact with an external surface of the fruit or vegetable 12 to be assessed.

Figure 1:
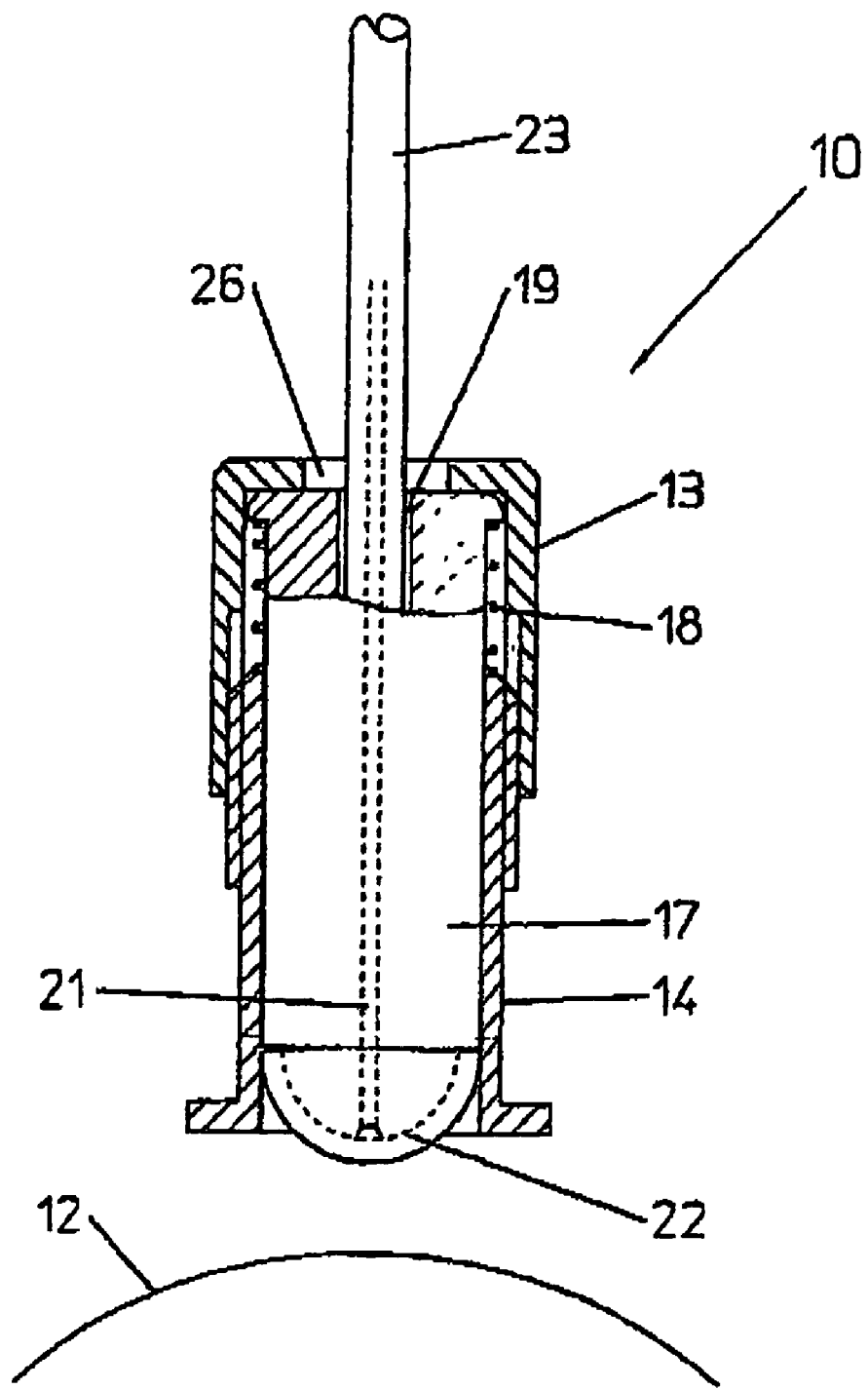
FIG. 1 shows a schematic representation of one embodiment, not to scale, of an assembly in accordance with the present invention.

The assembly 10 comprises a housing consisting of two interconnected parts 13, 14. Mounted within the housing is a moveable slug 17 which is moveable within the housing against the bias of a biasing member 18, preferably in the form of a spring. The slug 17 has an internal bore 19 through which extends an electrical connection, 21 into connection with a transducer, preferably formed by an active piezoelectric sensor 22, of generally curved, preferably hemispherical, form mounted at one end of the slug 17. The slug 17 is connected to a damping member 23 which extends through aligned apertures 19, 28 in the slug 17 and housing part 13 respectively. Conveniently, the electrical connection 21 will extend along side or within the damping member 23.

In use the assembly 10 is moved towards the surface of a fruit or vegetable 12 to be tested. As the assembly 10 contacts the surface of the fruit or vegetables 12, the momentum of the slug 17 causes the slug 17 to move, against the bias of the biasing means 18, to bring the piezoelectric sensor 22 into contact with a surface of the fruit or vegetable 12 being tested. It will be appreciated that by positioning the assembly of the invention an appropriate distance from the fruit or vegetables 12 to be tested it is possible for the movement of the sensor 22 after the assembly 10 has contacted the fruit or vegetable to be a tapping type of movement to the surface of the fruit or vegetable 12 being tested. It will be appreciated that such a tapping motion will not affect the condition of the fruit or vegetable being tested.

Because the piezoelectric sensor 22 has a curved surface, it is not necessary for the sensor 22 to contact with the surface of the fruit or vegetable being tested precisely perpendicularly to achieve accurate results using the assembly of the invention. The curvature of the sensor 22 means that good measurements can be achieved over a range of angles of contact with randomly curved surfaces of the fruit or vegetable 12 to be assessed. This means that it is not necessary for either the fruit being tested or the sensor assembly to be precisely aligned for the system to produce accurate results.

The piezoelectric sensor 22 generates a signal which is indicative of the condition of the fruit or vegetable 12. The signal from the piezoelectric sensor 22 is passed via the electrical connection 21 to suitable processing circuitry and possibly a display (not shown).

The assembly 10 is then retracted thereby moving the sensor 22 away from the fruit or vegetable 12. During this movement, once again movement of the slug 17 within the housing is biased by the biasing means 18.

Figure 2:
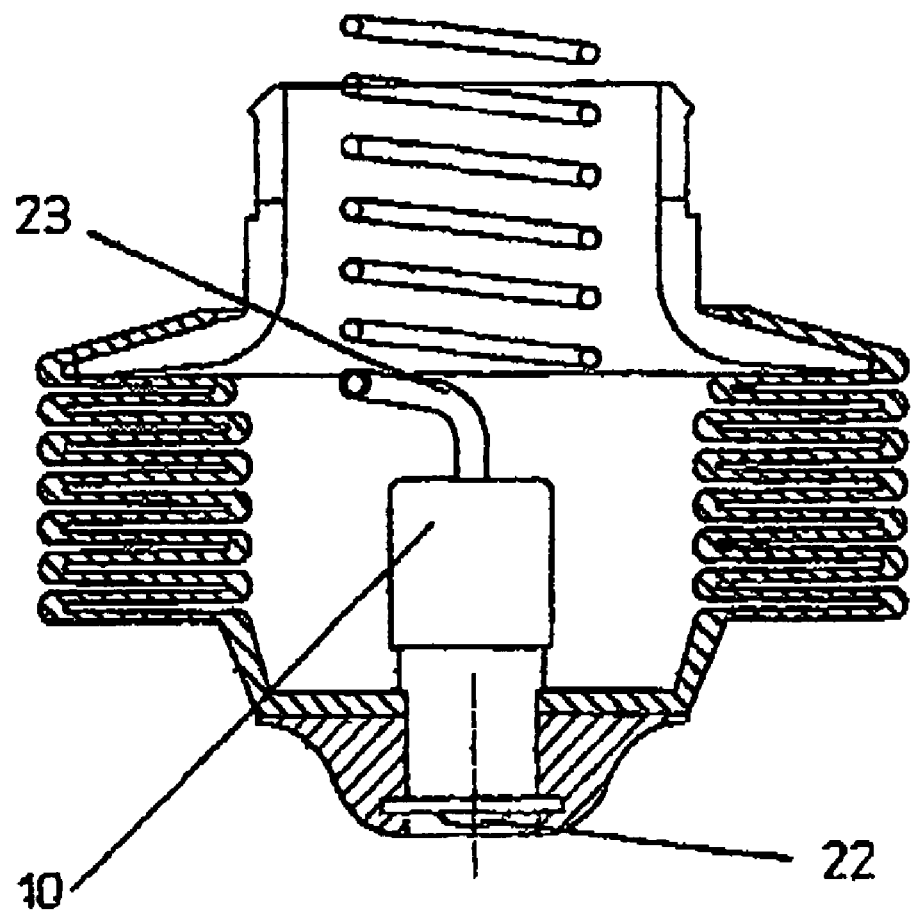
FIG. 2 shows a view, partly in section, of a preferred embodiment of assembly in accordance with the present invention, the assembly being mounted within a bellows arrangement.

Referring now to FIG. 2, there is shown an assembly of the type of FIG. 1 mounted in one suitable form of arrangement for moving the assembly 10 towards and away from the fruit or vegetable. Thus FIG. 2 shows an assembly 10 mounted within a bellows assembly of the type described in U.S. Pat. No. 4,217,164. The bellows assembly expands as pressurised air is introduced moving the assembly 10 towards, and into contact with, the surface of the fruit or vegetable 12. The assembly can then be retracted by introduction of a vacuum into the bellows which retracts the assembly 10 away from the surface of the fruit or vegetable 12 being tested. Further details of the bellows assembly, and its operation are described in detail in the abovementioned US patent, the contents of which are incorporated herein by reference.

The assembly 10 is preferably located internally of the bellows assembly and is mounted so as to be moveable therewith in any suitable manner.

It will be appreciated that the assembly of the invention makes it more simple to obtain consistent results without the need for absolute precision in setting up the assembly. It will be appreciated that it is important that accurate testing can be undertaken to prevent fruit or vegetables being incorrectly identified as to their condition.

It is of course to be understood that the invention is not intended to be restricted to the details of the above embodiments which are described by way of example only.

Thus, for example, whilst in the embodiment described, a bellows assembly is utilised to move the assembly towards and away from the fruit or vegetable's surface, it is to be appreciated that any other suitable mechanism can be used, as desired or as appropriate.

The invention claimed is:

1. Apparatus for measuring the condition of fruit and vegetables comprising a plunger movable into and out of contact with a surface of an item of fruit or vegetable,
said plunger carrying a transducer at a distal end thereof which is brought into contact with an item of fruit or vegetables, the transducer reacting to a property of said fruit or vegetables to produce an output signal related to that property,
wherein the transducer which contacts said item of fruit or vegetables is curved in shape.

2. Apparatus according to claim 1 mounted in a resilient bellows assembly, said bellows assembly being capable of expansion under the action of pressurized air to bring the transducer into contact with a fruit or vegetable surface for measurement, and retraction by the application of a vacuum to move the transducer away from the fruit or vegetable surface.

3. Apparatus according to claim 2 wherein the transducer comprises an active transducer.

4. Apparatus according to claim 3 wherein the transducer comprises a piezoelectric sensor.

5. Apparatus according to claim 4 wherein the transducer is generally hemispherical in shape at least at the part thereof which contacts the fruit or vegetable surface.

6. Apparatus according to claim 3 wherein the transducer is generally hemispherical in shape at least at the part thereof which contacts the fruit or vegetable surface.

7. Apparatus according to claim 2 wherein the transducer is generally hemispherical in shape at least at the part thereof which contacts the fruit or vegetable surface.

8. Apparatus according to claim 1 wherein the transducer comprises an active transducer.

9. Apparatus according to claim 8 wherein the transducer comprises a piezoelectric sensor.

10. Apparatus according to claim 9 wherein the transducer is generally hemispherical in shape at least at the part thereof which contacts the fruit or vegetable surface.

11. Apparatus according to claim 8 wherein the transducer is generally hemispherical in shape at least at the part thereof which contacts the fruit or vegetable surface.

12. Apparatus according to claim 1 wherein the transducer is generally hemispherical in shape at least at the part thereof which contacts the fruit or vegetable surface.

13. Apparatus according to claim 1 wherein the plunger comprises a housing within which is mounted a slug which carries said transducer wherein said slug is movable in said housing against the bias of a biasing member.

14. Apparatus according to claim 13 wherein the biasing means comprises a spring.

15. Apparatus according to claim 14 wherein said transducer is electrically connected by an electrical connection and said electrical connection is associated with or disposed within a damping member.

16. Apparatus according to claim 13, wherein movement of said slug in said housing is additionally damped by a damping member.

17. Apparatus according to claim 16 wherein said transducer is electrically connected by an electrical connection and said electrical connection is associated with or disposed within said damping member.

18. Apparatus according to claim 14, wherein movement of said slug in said housing is additionally damped by a damping member.

19. Apparatus according to claim 18 wherein said transducer is electrically connected by an electrical connection and said electrical connection is associated with or disposed within said damping member.

20. Apparatus according to claim 13 wherein said transducer is electrically connected by an electrical connection and said electrical connection is associated with or disposed within a damping member.

* * * * *